| United States Patent [19] | [11] | 4,137,631 |
|---|---|---|
| Pickett et al. | [45] | Feb. 6, 1979 |

[54] DISPOSABLE BLADE HOLDER

[75] Inventors: John E. P. Pickett, Durham, N.C.; Burton P. Franklin, Danville, Va.

[73] Assignee: Triangle Biomedical Equipment, Inc., Durham, N.C.

[21] Appl. No.: 877,468

[22] Filed: Feb. 13, 1978

[51] Int. Cl.² ............................................. B26B 1/00
[52] U.S. Cl. ....................................... 30/337; 30/329
[58] Field of Search .................................. 30/337, 329

[56] References Cited

U.S. PATENT DOCUMENTS

| 1,827,509 | 10/1931 | Ericsson | 30/329 |
| 2,479,788 | 8/1949 | Stokes | 30/337 |
| 2,631,372 | 3/1953 | Fournier | 30/329 |

FOREIGN PATENT DOCUMENTS

| 488796 | 12/1952 | Canada | 30/337 |
| 882966 | 7/1953 | Fed. Rep. of Germany | 30/329 |
| 120242 | 11/1947 | Sweden | 30/329 |

*Primary Examiner*—James L. Jones, Jr.
*Assistant Examiner*—J. T. Zatarga
*Attorney, Agent, or Firm*—B. B. Olive

[57] ABSTRACT

A disposable blade holder includes a comfortably fitting handle portion and a blade clamping portion adapted to securely lock one end of a disposable blade in angular relation to the handle portion, the blade being of the precision ground, single edge, unbanded, notched end type as employed for surgical preparation, disposable microtome blade cutting operations, and the like.

1 Claim, 6 Drawing Figures

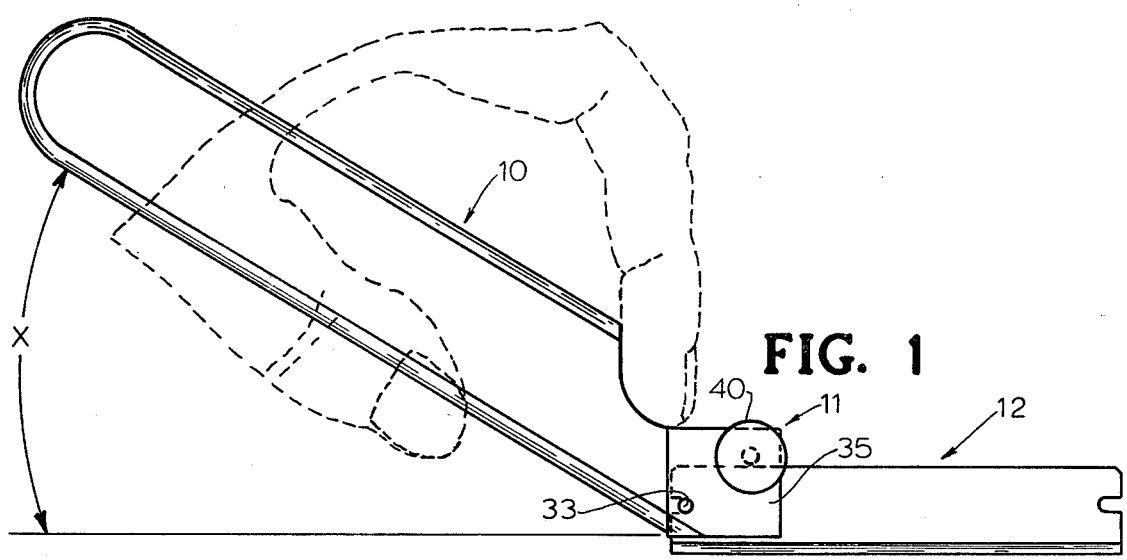
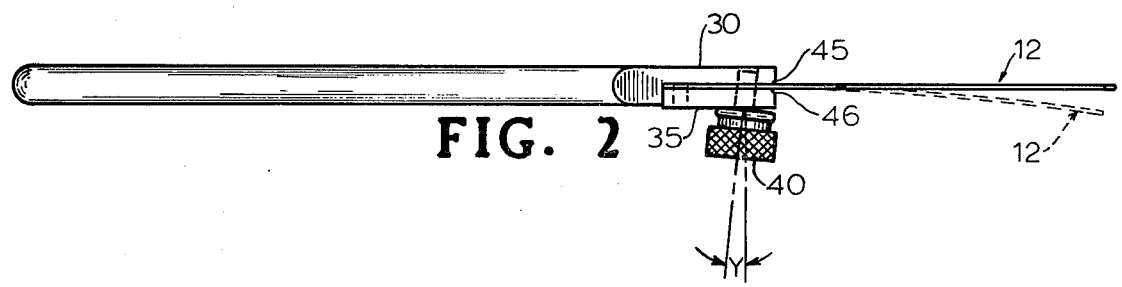
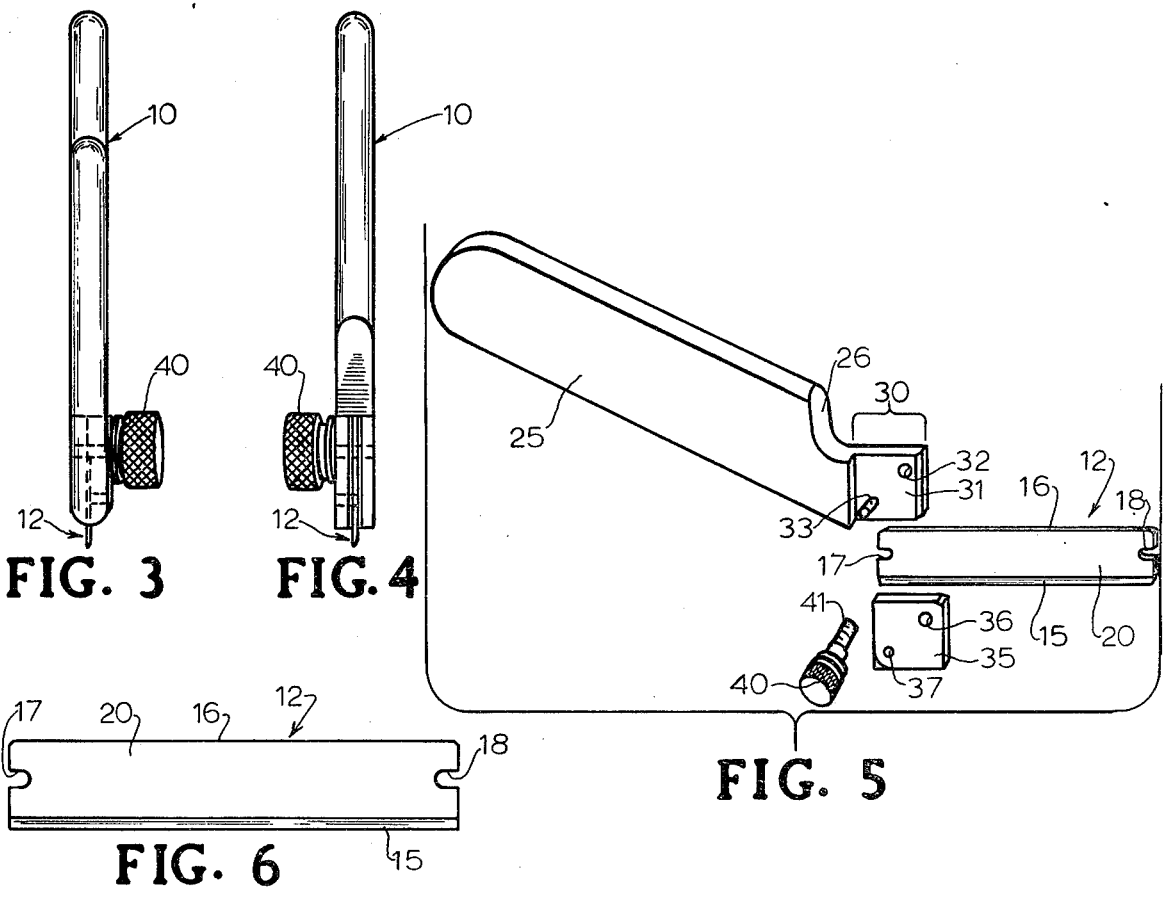

4,137,631

DISPOSABLE BLADE HOLDER

BACKGROUND OF THE INVENTION

1. Field of the Invention

The invention relates to disposable blade holders.

2. Description of the Prior Art

Precision ground, single edge disposable blades have long been used for surgical preparation and similar applications. In some instances, such single edge blades have been provided with a band, i.e., a bent metal strip, over the unsharpened edge to facilitate use. In other instances, the unsharpened edge has been unbanded. Also, some of such blades have notched ends while others have been sold and used with unnotched ends.

A relatively recent development is described in U.S. Pat. No. 3,699,830 relating to the employment of precision ground, single edge, unbanded, notched end type disposable blades in laboratory microtomes for the precision cutting of tissue sections. Such blades are typically made of a very fine grade of steel and are adapted to receive an extremely sharp cutting edge. After repeated use in microtome cutting operations, the cutting edge eventually develops minor flaws and at this point the blade must be replaced. However, a used blade of this type still has a relatively high cutting capability with a sharpness entirely adequate for a variety of manual cutting operations, e.g., the trimming of gross tissue into small blocks for further processing in histology laboratories.

Due to the unavailability of a satisfactory blade holder to permit further utilization of these high grade, relatively expensive blades, they have usually been discarded when no longer suitable for use in the microtome cutting. This, of course, has been a wasteful practice.

Representative examples of prior art disposable blade holders are to be found in U.S. Pat. Nos. 1,865,539; 1,998,428; 2,232,008 and 3,227,020. However, insofar as we are aware, there has never been made available a satisfactory blade holder adapted for use with a disposable, precision ground, single edge, unbanded, notched end type. More specifically, there is no known practical blade holder for holding this type of disposable blade in a proper cutting angle for conducting manual cutting operations in histology procedures, and the like, as well as being useful for other day-to-day cutting, scraping, cleaning operations, and the like, as might be encountered in the household, for example.

Thus, the object of the present invention is to provide a versatile, disposable blade holder, particularly adapted for comfortably holding at a proper angle one end of a disposable, precision ground, single edge, unbanded, notched end type blade.

SUMMARY OF THE INVENTION

According to the invention, there is provided a disposable blade holder adapted to securely hold a precision ground, single edge, unbanded, notched end type blade in proper position for conducting manual cutting, scraping, and like operations. The blade holder comprises a handle member and a unique means for clamping and locking the end of the blade in a proper cutting position. The handle member is shaped to fit comfortably in the hand when gripped and is provided with an indentation at its lower end for positioning the forefinger to guide the instrument during use.

Contiguous with the handle indentation and angularly disposed in a forward direction therefrom is a rectangularly-shaped blade receiving member having a flat, clamping surface. The blade receiving member is oriented with respect to the handle such that when its bottom edge is positioned on a horizontal surface, the handle member extends upwardly from the surface and forms an included angle of from 25° to 40° therewith. The inner clamping surface of the blade receiving member is provided with a pin for positioning a notched end of the blade and also includes a threaded hole for receiving a thumbscrew. Once the blade is positioned, a cap having the same shape and dimensions as the blade receiving member is fitted over the blade receiving member and clamped by means of a thumbscrew which locks the blade receiving member and mating cap together and secures the end of the blade in place ready for use.

DESCRIPTION OF THE DRAWINGS

FIG. 1 is a side view of an assembled blade holder made according to the invention and depicting in dotted lines typical finger positions.

FIG. 2 is a top view of the assembled blade holder with a flexed position indicated in dashed lines.

FIG. 3 is a rear view of the assembled blade holder.

FIG. 4 is a front view of the assembled blade holder.

FIG. 5 is an exploded view of the blade holder and blade components making up the assembly.

FIG. 6 is a side view of the type disposable blade adapted for use with the invention.

DESCRIPTION OF THE PREFERRED EMBODIMENT

A complete disposable blade assembly according to the invention includes a handle portion 10, a blade end clamping portion 11 and the blade 12. As best seen in FIG. 6, the type of disposable blade intended for use with the holder of the invention is characterized by having a precision ground edge 15, an opposite unbanded edge 16, a pair of end notches 17, 18, and a generally rectangular body.

The handle portion 10 is characterized by having an elongated bar-like handle 25 with a forwardly located depression 26 and integral therewith a rectangular clamp portion 30 having a rectangular bearing surface 31 and generally aligned along a diagonal of said surface 31 a threaded hole 32 and a pin 33.

A rectangular clamping plate 35 mates the clamping portion 30 of handle 10 and includes an unthreaded hole 36 mating threaded hole 32 and a hole 37 adapted to slidably receive pin 33. A thumbscrew 40 is adapted to pass through hole 36 and thread into hole 32 for purposes of clamping plate 35 to clamp portion 30 of handle 10. The thumbscrew 40 is angularly related to the blade receiving member to increase unit area pressure on the plate 35 and which also makes it easier to break the pressure. A slight angle Y of about 5° off the plate member perpendicular axis appears sufficient and holes 32 and 36 are angled accordingly.

While it is believed the figures are generally self-explanatory, it will be noted that one of the notched ends, 17 or 18, of blade 12 is fitted to engage pin 33 and with the edge 15 of blade 12 directed downwardly.

Plate 35 is mated with the clamp portion 30 of handle 10 by passing pin 33 through hole 37 and directing the threaded portion 41 of thumbscrew 40 through hole 36 and into the threaded hole 32 such that the upper unbanded edge 16 of blade 12 bears against the stem portion of thumbscrew 40. Also to be noted is that when the holder of the invention is held in the position depicted in FIG. 1, the cutting edge 15 has an angular relation to the handle 10 as represented by the angle X which should preferably be in the range of 25° to 40° which represents the angle between the bottom edge of the mating clamp plate 35 and clamp portion 30 in relation to the bottom edge of the handle 10 as best shown in FIG. 1.

While the primary purpose of the invention has been to provide a practical blade holder suited to utilizing used disposable microtome blades of the type described for further gross cutting operations, it has been discovered that the blade holder of the invention also makes possible an improved cutting and scraping device for household applications such as for removing paint and the like. In this regard, it may be noted that the described type of blade exhibits some degree of flexibility as illustrated in FIG. 2 which adapts the holder of the invention to paint scraping and similar operations. Thus, the blade holder of the invention makes available a novel and practical disposable blade holder for general application. Also of advantage is the fact that once a blade 12 has been used to its fullest extent, a replacement blade can be inserted into the holder of the invention merely by loosening the thumbscrew 40 and inserting the replacement blade between the clamp portion 30 of handle 10 and the cap or plate member 35. This blade replacement procedure is facilitated by rounding the forward receiving edges 45, 46 of the respective mounting portion 30 and plate 35 as best seen in FIG. 2.

What is claimed is:

1. A blade holder for securely holding a flexible, rectangularly shaped, precision ground, single edge, notched end blade, said blade holder comprising:
  (a) an elongated handle member shaped to fit comfortably in the hand when gripped and containing a recess at the top of its lower end for receiving the forefinger;
  (b) a substantially rectangular shaped blade receiving member integral with and extending forward of said handle member and positioned in an angular relationship to said handle member such that the bottom edges of said handle member and said blade receiving member form an included angle in the range of from about 25° to 40°, and wherein said blade receiving member contains a threaded aperture in the forward top corner thereof and mounts an outwardly extending pin in the bottom rear corner thereof, with said pin being adapted to mate with a notch at one end of said blade for positioning said blade on said blade receiving member with the cutting edge thereof extending below the bottom edge of said blade receiving member;
  (c) a removable rectangular cap member adapted to fit over and mate with said blade receiving member with an end segment of said blade sandwiched therebetween, said removable cap being of the same shape and dimensions as said blade receiving member and having a first aperture adapted to slidably receive the pin attached to said blade receiving member to position said cap over said blade receiving member and a second aperture adapted for alignment with the threaded aperture of said blade receiving member when said cap is in engagement with said pin; and
  (d) a threaded thumbscrew angularly disposed relative to said blade receiving member by having the axis of said thumbscrew angled away from an axis perpendicular to the face of said cap member and adapted to securely clamp said blade between said blade receiving member and said cap when inserted through said cap second aperture and tightened into said blade receiving member threaded aperture.

* * * * *